(12) United States Patent
Tang et al.

(10) Patent No.: US 8,750,957 B2
(45) Date of Patent: Jun. 10, 2014

(54) MICROFABRICATED NEURAL PROBES AND METHODS OF MAKING SAME

(75) Inventors: Hongxing Tang, New Haven, CT (US);
Michael L. Roukes, Pasadena, CA (US);
Richard Renaud, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 1292 days.

(21) Appl. No.: 11/628,003

(22) PCT Filed: Jun. 1, 2005

(86) PCT No.: PCT/US2005/019190
§ 371 (c)(1),
(2), (4) Date: Jan. 14, 2008

(87) PCT Pub. No.: WO2005/117554
PCT Pub. Date: Dec. 15, 2005

(65) Prior Publication Data
US 2008/0255439 A1    Oct. 16, 2008

Related U.S. Application Data

(60) Provisional application No. 60/575,991, filed on Jun. 1, 2004.

(51) Int. Cl.
*A61B 5/04* (2006.01)
*A61N 1/00* (2006.01)

(52) U.S. Cl.
USPC ............ 600/378; 600/372; 600/545; 607/116

(58) Field of Classification Search
USPC ........... 600/372–374, 378, 544–547; 607/116
See application file for complete search history.

(56) References Cited

U.S. PATENT DOCUMENTS

| 5,215,088 | A | * | 6/1993 | Normann et al. ............. 600/377 |
| 5,388,577 | A | | 2/1995 | Hubbard et al. |
| 5,513,636 | A | | 5/1996 | Palti |
| 6,719,582 | B1 | | 4/2004 | Swanson |
| 2002/0166962 | A1 | | 11/2002 | Roukes et al. |
| 2003/0062193 | A1 | | 4/2003 | Thaysen et al. |

(Continued)

FOREIGN PATENT DOCUMENTS

| WO | WO 03/095616 A2 | 11/2003 |
| WO | WO 03/095617 A2 | 11/2003 |
| WO | WO 2004/041998 A2 | 5/2004 |

OTHER PUBLICATIONS

"Electric-field-mediated inhibition of cell and microparticle adhesion: a new way to create bio-repellent surfaces" Fuhr et al. 1995.*

(Continued)

*Primary Examiner* — Linda Dvorak
*Assistant Examiner* — Brian M Antiskay
(74) *Attorney, Agent, or Firm* — The Marbury Law Group, PLLC

(57) ABSTRACT

An embodiment of the invention provides a neural probe containing a plurality of nanoscale recording electrodes. The recording electrodes have a width of 1 micron or less and a distance between adjacent recording electrodes is 10 microns or less. Another embodiment of the invention provides a neural probe comprising a plurality of microfabricated recording electrodes located on a polymer base material, such as a flexible polymer cantilever.

16 Claims, 18 Drawing Sheets

(56) References Cited

U.S. PATENT DOCUMENTS

| | | |
|---|---|---|
| 2003/0089182 A1 | 5/2003 | Thaysen et al. |
| 2003/0100823 A1 | 5/2003 | Kipke et al. |
| 2005/0034529 A1 | 2/2005 | Tang et al. |
| 2005/0150280 A1 | 7/2005 | Tang et al. |

OTHER PUBLICATIONS

Thaysen et al., "Polymer-Based Stress Sensor With Integrated Readout," Journal of Physics D: Applied Physics, vol. 35, Institute of Physics Publishing Ltd., 2002, pp. 2698-2703.

* cited by examiner

PRIOR ART

FIGURE 6D
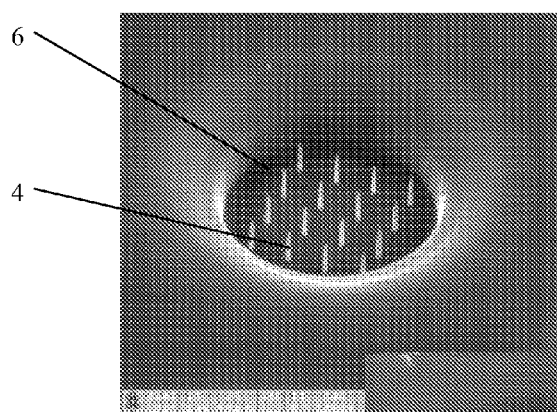
FIGURE 6E
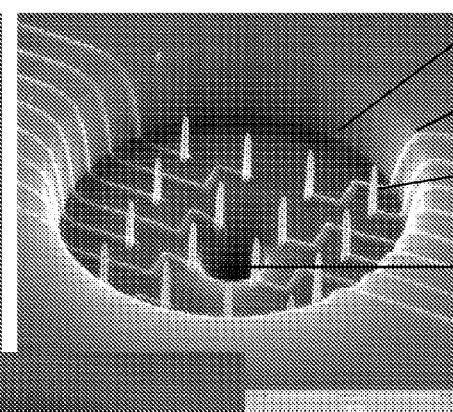
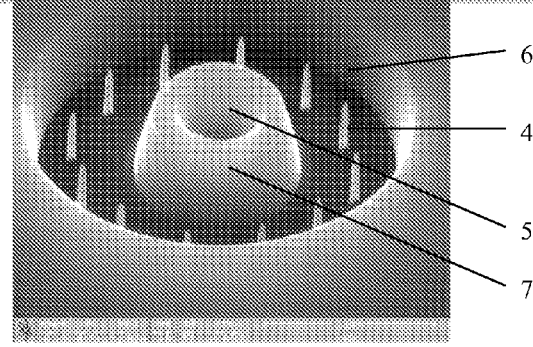
FIGURE 6F

FIGURE 13A
FIGURE 13B
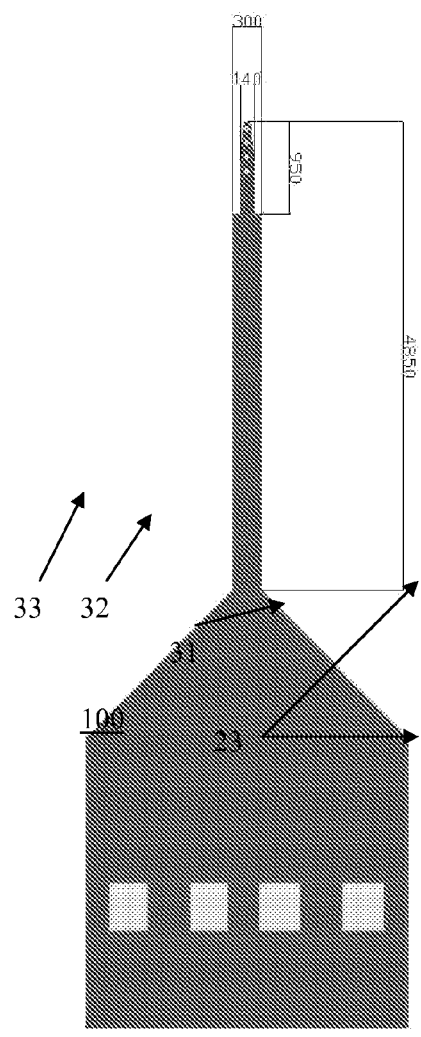
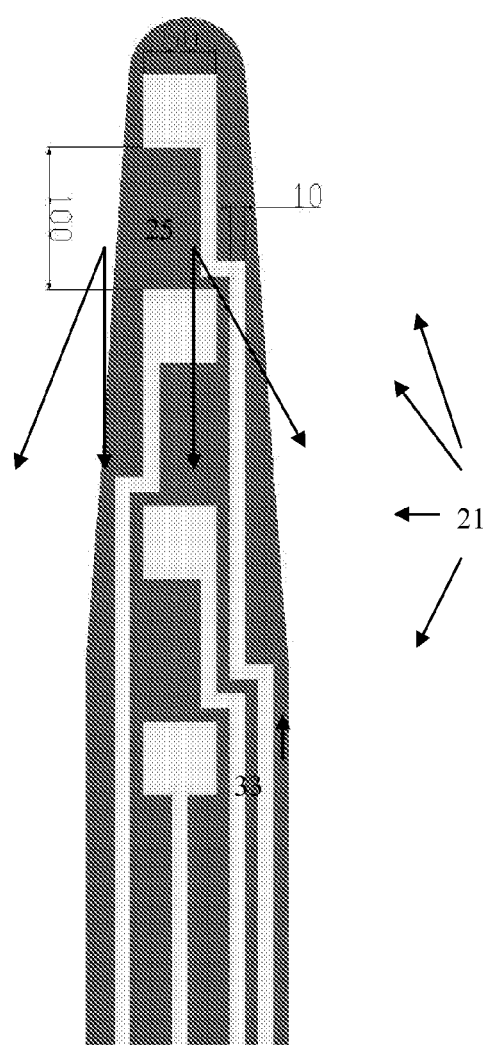

MICROFABRICATED NEURAL PROBES AND METHODS OF MAKING SAME

This application claims benefit of priority of U.S. Provisional Application Ser. No. 60/575,991 filed Jun. 1, 2004, which is incorporated herein by reference in its entirety.

BACKGROUND OF THE INVENTION

1. Field of the Invention

The invention is related to micro-electro-mechanical systems (MEMS) and methods of making these systems.

2. Description of the Prior Art

In neurobiology, to study the central nervous system, electro physiologists use electrodes (referred to herein as recording electrodes) placed in the extra-cellular medium to record the activity of multiples neurons simultaneously. The variation of the local electrical potential is detected or recorded due to the action potentials (spikes) occurring in the surrounding neurons. By using more than one electrode, it is then possible to distinguish action potentials coming from different neurons due to the variation of the shape of the spike while traveling in the extracellular media. This way, each neuron firing will have a distinctive signature of spikes on the multiples electrodes as illustrated in FIG. 1.

The problem of associating a specific spike's signature on the electrodes to a specific neuron is called spike sorting. While simple tetrodes made of wires twisted together have been and are still in use, micro-machined electrode arrays are now becoming more and more common. Their main advantages are the consistency from one probe to the other compared to manually fabricated probes and the control over the dimensions and spacing of multi electrodes.

The micromachined neural probes have limited spatial resolution. The distance between recording pads are larger than 20 microns, which is generally larger than the size of neurons. The present inventors realized that these probes cannot be effectively utilized to probe neighboring neurons. Furthermore, the present inventors realized that these probes are more expensive than desired because they are made using expensive silicon processing steps, such as reactive ion etching (RIE) and plasma-enhanced chemical vapor deposition (PECVD).

BRIEF SUMMARY OF THE INVENTION

An embodiment of the invention provides a neural probe containing a plurality of nanoscale recording electrodes. The recording electrodes have a width of 1 micron or less and a distance between adjacent recording electrodes is 10 microns or less. Another embodiment of the invention provides a neural probe comprising a plurality of microfabricated recording electrodes located on a polymer base material, such as a flexible polymer cantilever.

BRIEF DESCRIPTION OF THE DRAWINGS

FIGS. 6A, 6B, 6C, 6D, 6E and 6F are SEM images of electron beam deposited recording electrodes.

FIG. 7A shows a silicon wafer covered by 50 Å Cr/500 Å Au/200 Å Cr release layer.

FIG. 7B shows spinning of a 0.5 μm thick layer of SU-8 2000.5.

FIG. 7C shows exposure and development of the SU-8 2000.5 layer.

FIG. 7D shows photoresist spinning and patterning metal interconnection.

FIG. 7E shows thermal evaporation of a 50 Å Cr adhesion layer and of a 0.1 μm Au layer.

FIG. 7F shows lift-off of the Cr/Au to form the metallic interconnection, linking bonding pads to recording pads.

FIG. 7G shows spinning of a 10 μm thick layer of SU-8 2010.

FIG. 8A shows exposure and development of the SU-8 2010.

FIG. 8B shows spinning of a 100 μm thick layer of SU-8 2100.

FIG. 8C shows exposure and development of the SU-8 2100.

FIG. 8D shows the final probe released from the wafer by a chrome etch.

FIG. 9A shows a silicon wafer covered with thermally evaporated 50 Å Cr/500 Å Au/200 Å Cr release layer.

FIG. 9B shows deposition of 0.5 μm of Parylene-C.

FIG. 9C shows photoresist spinning and patterning for first etching mask.

FIG. 9D shows thermal evaporation of 2000 Å of aluminum.

FIG. 9E shows lift-off of the aluminum in acetone to form the first etching mask.

FIG. 9F shows etching of the Parylene-C through the first aluminum mask with oxygen plasma (200 mT, 400 W) at a rate of 0.2 μm/hour.

FIG. 10A shows removal of the first aluminum mask, leaving only the cover layer of the neural probe.

FIG. 10B shows photoresist spinning and patterning for connecting lines, connecting pads and recording pads.

FIG. 10C shows thermal evaporation of a 50 Å Cr adhesion layer and of a 0.1 μm Au layer.

FIG. 10D shows lift-off of the gold to form the connecting lines, connecting pads and recording pads.

FIG. 10E shows deposition of 10 μm of Parylene-C.

FIG. 10F shows photoresist spinning and patterning for second etching mask.

FIG. 11A shows thermal evaporation of 2000 Å of aluminum.

FIG. 11B shows lift-off of the aluminum in acetone to form the second etching mask.

FIG. 11C shows etching of the Parylene-C through the second aluminum mask with oxygen plasma (200 mT, 400 W) at a rate of 0.2 μm/hour.

FIG. 11D shows removal of the second aluminum mask, leaving only the cantilever body of the neural probe as well as a protecting layer for the connecting lines.

FIG. 12A shows spinning and patterning of a 100 μm SU-8 2100 handle.

FIG. 12B shows release of the probe from the wafer by etching the Cr release layer.

FIG. 13A is a schematic top view of outside dimensions, in microns, of a probe of the second embodiment, including SU-8 handle, the gold pads and the SU-8 or parylene cantilever.

FIG. 13B is a schematic top view of inside dimensions at the very tip, in microns, of the probe of the second embodiment, including the gold pads, connecting lines and the 10 μm thick SU-8 or parylene cantilever.

DETAILED DESCRIPTION OF THE INVENTION

1. First Embodiment

In a first embodiment of the invention, the present inventors have developed a method to fabricate a neural probe which contains a plurality of nanoscale recording electrodes. Preferably, the recording electrodes have a width of 1 micron or less, such as about 0.1 to about 0.8 microns, form example about 0.3 to about 0.5 microns. It should be noted that while the electrodes preferably have a round cross section where the width of the electrodes refers to their diameter, they may also have polygonal or irregular cross section, where the width refers to the maximum width of the electrodes. The electrodes may have any suitable height, such as 6 microns or less, for example 2 to 5 microns.

Preferably, a distance between adjacent recording electrodes is 10 microns or less, such as 1 to 4 microns, for example. The probe electrode density is preferably about 1/10 nm squared to about 1/50 nm squared. The electrode width and spacing is designed to allow the probe to accurately and separately measure the activity (i.e., firing) of adjacent or neighboring neurons and/or to even measure the activity of the same neuron with different electrodes.

The electrodes may be formed on any suitable substrate, such as a semiconductor (including silicon), insulating (including polymer, glass, silicon oxide, silicon nitride, ceramic, etc) or conductive (including metal and conductive metal oxide) substrate. The substrate preferably comprises a cantilever (i.e., beam), but may comprise other shapes, such as diaphragm or block shapes.

The probe may be made by any suitable microfabrication method. Preferably, the electrodes are formed by electron beam assisted deposition. The probe components may be formed by electron and ion beam deposition. FIGS. 2-5 illustrate a non-limiting example for a probe of the first embodiment.

The exemplary probe was fabricated for convenience upon a pre-existing commercial neural probe fabricated by MEMS processes. However, it should be understood that the probe can be formed on a new substrate rather than over an existing probe with larger electrode width and spacing. The probe components, such as pads and electrodes are deposited in a FEI NOVA 600 dual focused ion beam/electron beam system. These smaller and denser recording pads and electrodes allow probing the electrical activities of neighboring neurons and even the same neuron.

Figure 1:
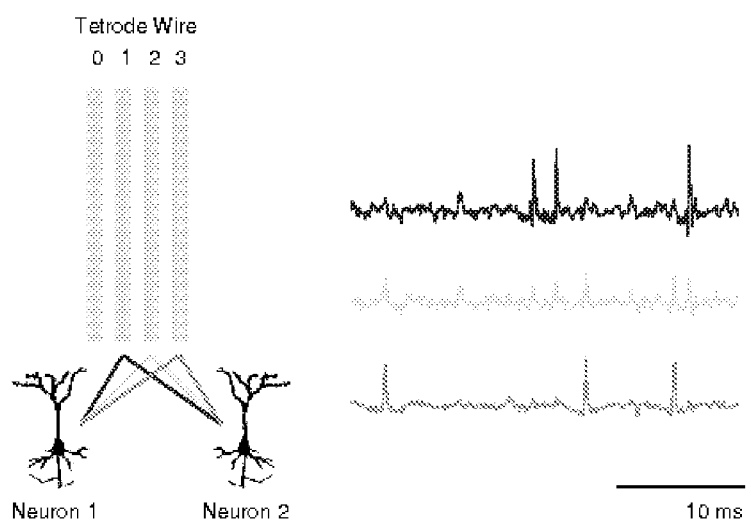
FIG. 1 is an illustration of prior art spike sorting. A neuron will leave a somehow smaller spike on an electrode further away from the neuron than on one closer to the neuron. Using multiple electrodes it is then possible to identify whether the spikes are emitted from the same neuron or from different ones.
Figure 2:
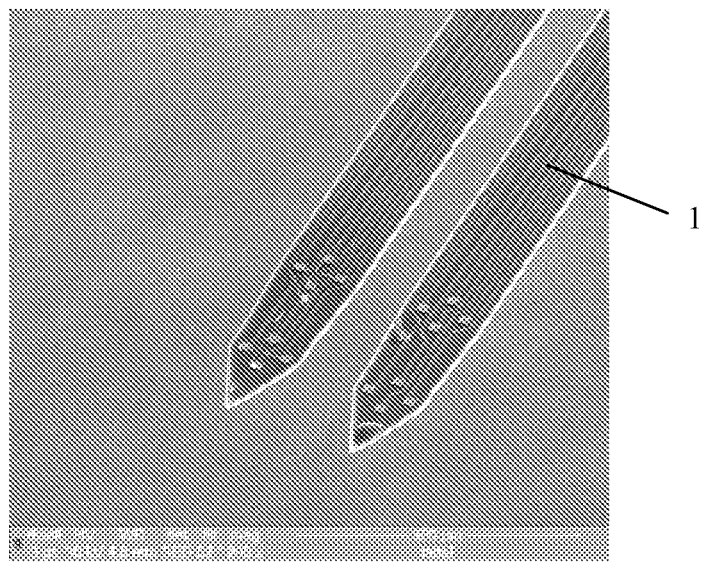
FIG. 2 is an SEM image of a commercial neural probe used as starting substrate in the first embodiment.
Figure 3:
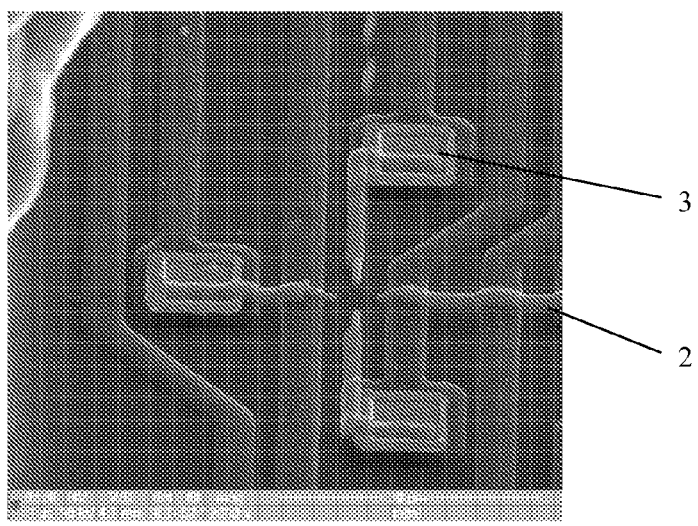
FIG. 3 is an SEM image of deposition of connecting Pt lines through ion-beam deposition. These serve as interconnection from the existing micro-scale recording pad to the nanoscale recording site to be deposited in the next step.

A commercial tetrode, a 2×2-tet from NeuroNexus Technologies is used as starting substrate 1 for convenience, as shown in FIG. 2. Then, connections 2 (i.e., connecting lines) are formed from the existing recording pads 3 on the probe to a space between the existing pads, as shown in FIG. 3. These connections are formed by using the ion beam and a carbon-platinum gas mixture to plate the platinum based connections. Other conductive materials may be used instead. The connections may be formed in two or more steps such that the connection width decreases closer to the electrode location. A conductive pad or base at the electrode location may also be formed for easier electrode fabrication.

An electron beam, which has a smaller spot size than the ion beam, is then used to deposit the recording electrodes 4 in electrical contact with the connections. The same mixture of carbon-platinum from a gas needle in the apparatus is provided into the electron beam to create elevated recording electrodes of about 6 μm height, similar to the ones shown in FIG. 4. Metals other than Pt may also be used for the electrodes. Preferably, the tips of the electrodes are sharpened by focused ion beam milling or other etching methods for easy access to cell membranes. These recording electrodes may be used to probe the extracellular medium of neurons at different depth in the tissues simultaneously. The resistance from the electrode tips to the bonding pads is relatively small, such as about 1 kOhm.

Figure 5:
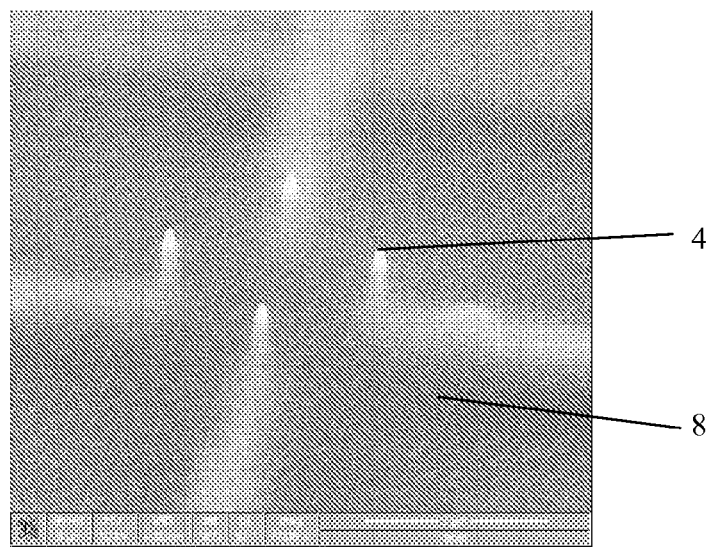
FIG. 5 is an SEM image of an insulating layer applied and windows opened at the top of the electrodes by ion milling or oxygen plasma etching of the top insulating layers.

As a final step, a 0.5 μm thick insulation layer 8 of SU-8 is formed over the electrodes by spin coating or other techniques. Alternatively, other insulating materials, such as polymers (including parylene) and glass (including FOX spin on glass) may be used instead. The insulating layer is then etched back at the tip of the probe by milling with the ion beam, oxygen plasma etching or other methods, to expose the elevated recording electrodes, as shown in FIG. 5.

Figure 6A:
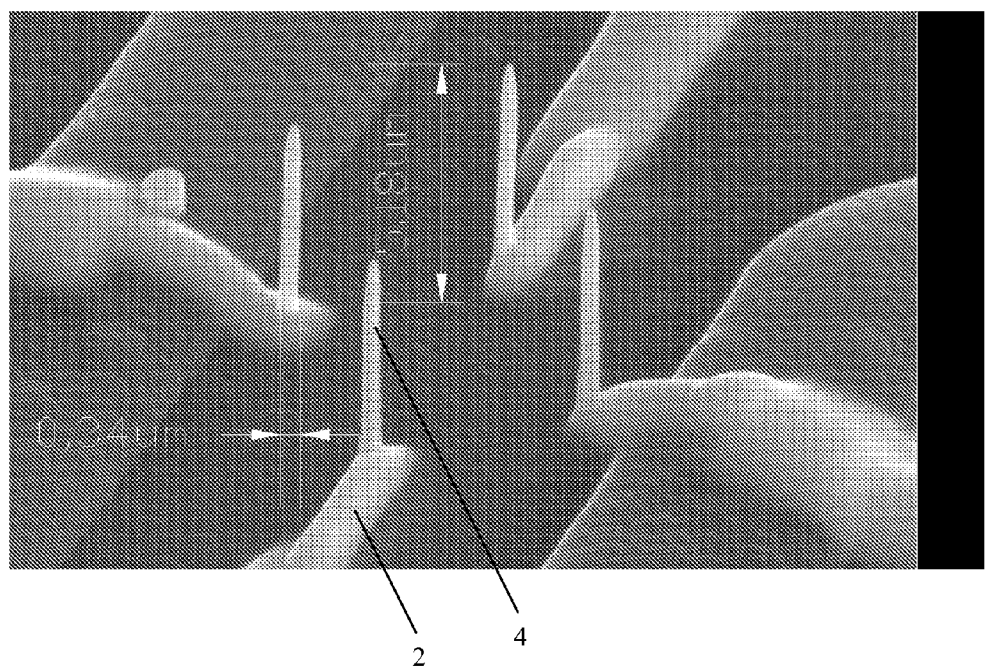

The dimensions for the probe are illustrated in FIG. 6A. For example, the electrodes are 0.34 microns wide and 5.18 microns wide.

Figure 4:
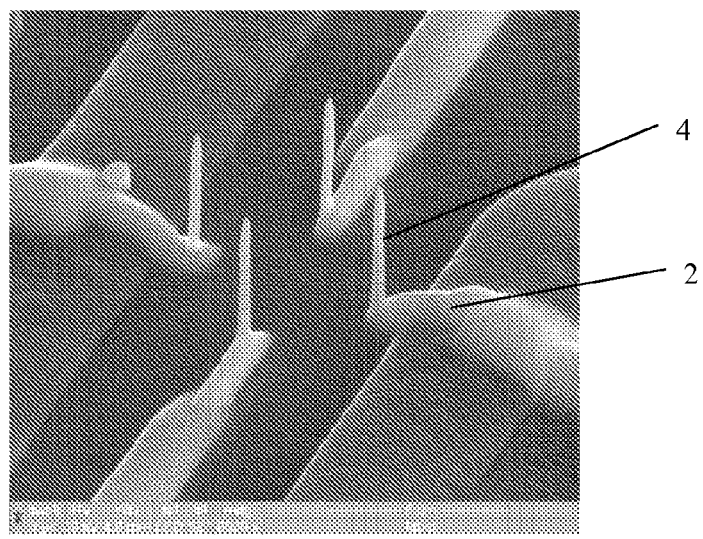
FIG. 4 is an SEM image of electron beam deposited, elevated nanoscale recording electrode.
Figure 6B:
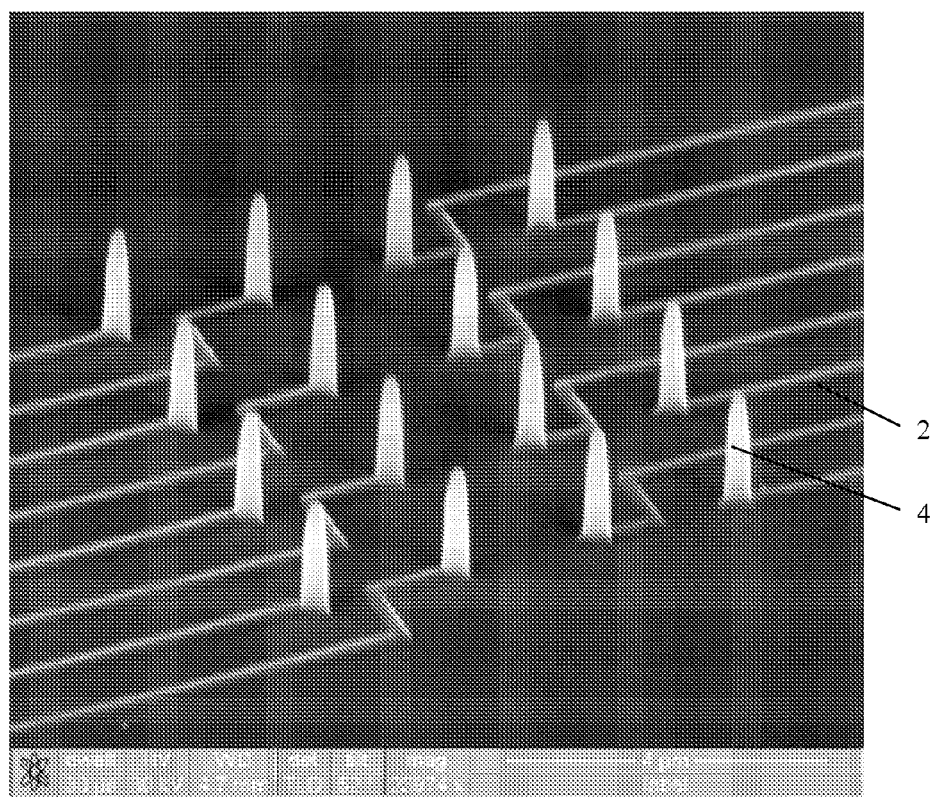
Figure 6C:
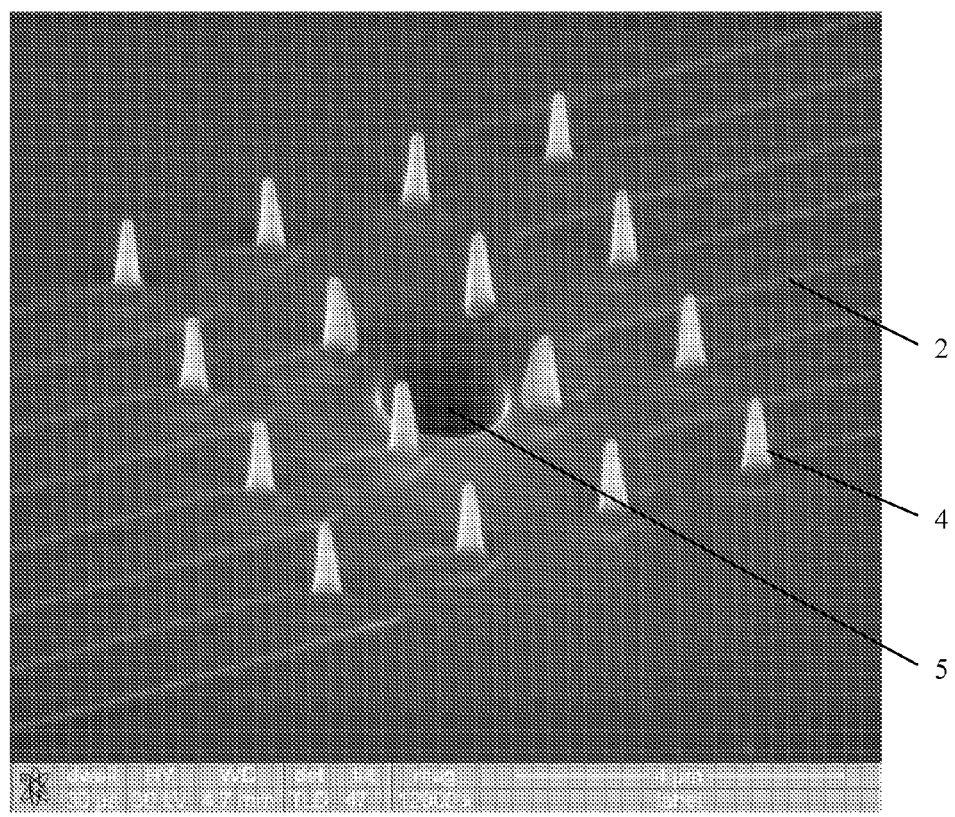

It should be noted that the recording electrodes do not have to be configured in a tetrode configuration shown in FIG. 4. For example, FIG. 6B shows a multi-electrode array with a high density of connecting lines located on a substrate. If desired, holes 5 in the probe base or substrate material, such as a cantilever, may be provided between the electrodes, as shown in FIG. 6C. The holes may be used to create a suction to draw the cells in contact with the probe base or substrate material and facilitate contact between the cell membrane and the electrodes. If desired, the holes may be connected to a micropump or other suction causing devices in order to generate a suction force at the holes.

Furthermore, the electrodes may be located in a recess 6 in the probe base or substrate material as shown in FIGS. 6D, 6E and 6F. The recess is shaped and sized to facilitate the contact between the cell and the electrodes. If desired, the suction hole may be located in the recess, as shown in FIGS. 6E and 6F. In FIG. 6F, the suction hole is located in a pillar or protrusion 7 rising out of the recess containing the electrodes in order to facilitates the suction of the cells to the probe. Thus, the first embodiment provides a probe containing recording electrodes for electrophysiology and neurology detection, such as for neuron firing detection.

2. Second Embodiment

The second embodiment provides a neural probe comprising a plurality of microfabricated recording electrodes located on a polymer base material. Preferably, the recording pads containing the electrodes are located on and/or are partially encapsulated in a flexible cantilever shaped polymer structure. The preferred polymer materials are SU-8 and parylene. However, other materials may also be used. The second embodiment also provides a method of making a neural probe which includes forming a polymer support structure and forming conductors encapsulated in the polymer support structure. The conductors electrically connect exposed electrically addressable metal pads to a plurality of recording electrodes to form the neural probe.

In a first aspect of the second embodiment, the electrodes are located on the SU-8 polymer material. SU-8 is a negative tone, near UV photo-resist. Its properties allow building s structure from 0.5 µm to 300 µm thick. The advantages of building a probe with SU-8 are the simplicity of the processing steps that make them cheaper to produce than silicon based probes.

Figure 7A:
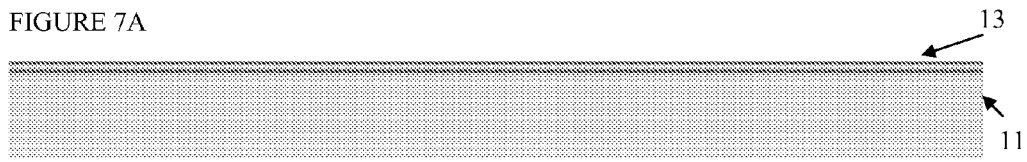
FIGS. 7A-7G and 8A-8D are side cross sectional views of steps in a method of microfabricating a neural probe of the second embodiment.
Figure 7B:
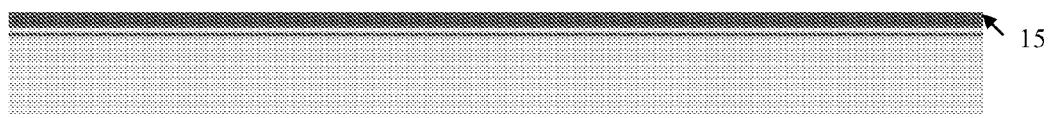
Figure 7C:
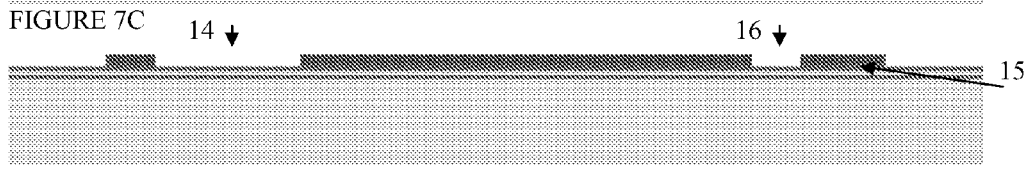

The process flow illustrating the general fabrication process of a SU-8 based neural probe is shown in FIGS. 7A to 8D, each picture representing a processing step. FIG. 7A shows a substrate 11, such as a 750 micron silicon wafer covered by 50 Å Cr/500 Å Au/200 Å Cr release layer 13. Any other suitable substrate material, such as glass, quartz, ceramic, other semiconductors, metal, etc. may be used instead. The films in layer 13 may be formed by any suitable thin film deposition method. Other suitable release layer material or materials as well as layer thicknesses may be used instead. FIG. 7B shows spinning of a 0.5 µm thick polymer layer 15 which comprises SU-8 2000.5. Other suitable thicknesses, such as 0.25 to 1 microns, for example may also be used. Layer 15 may be deposited as follows: spin up to 500 rpm at 100 rpm/s for 5 seconds then up to 3000 rpm at 300 rpm/s for 30 seconds, followed by a soft bake at 105° C. for 60 seconds. FIG. 7C shows exposure and development of the SU-8 2000.5 layer 15 using photolithography. Layer 15 contains openings 14 and 16 where the metal contact (i.e., bonding) and recording pads, respectively, will be formed in a later step. The exposure may comprise a 150 mJ/cm$^2$ for 6 seconds exposure through a mask followed by a post bake at 105° C. for 60 seconds, avoid rapid cooling. The development may comprise development in an SU-8 developer for 30 seconds followed by a rinse in IPA.

Figure 7D:
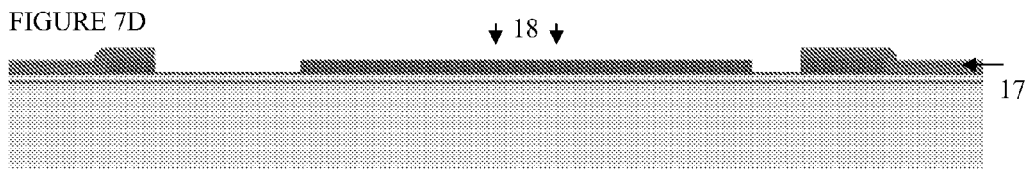
Figure 7E:
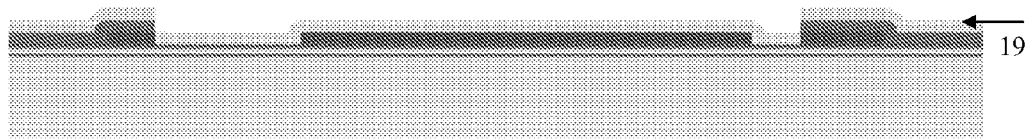
Figure 7F:
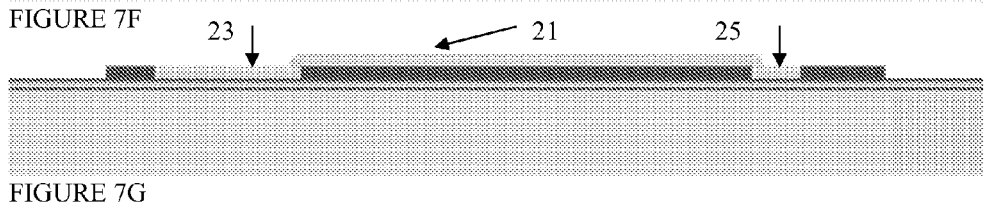

FIG. 7D shows photoresist spinning and patterning metal interconnection. Specifically, a photosensitive layer 17, such as a photoresist, is spun over the substrate 11 and over the developed (i.e., patterned) polymer layer 15. The photosensitive layer 17 is then photolithographically exposed and developed to form an opening 18 where the metal interconnections, contact pads and recoding pads would be located. FIG. 7E shows the deposition of a metal connection (i.e., interconnect) material 19 over the patterned photosensitive layer 17. For example, the connection material 19 may be formed by thermal evaporation of a 50 Å Cr adhesion layer and of 0.1 µm Au layer. FIG. 7F shows lift-off of the Cr/Au layer 19 to form the metallic interconnections 21 linking the contact pads 23 to recording pads 25 upon which the recording electrodes will be formed.

The following exemplary lift-off process may be used. PMGI SF-9 resist is spun up to 500 rpm at 100 rpm/s for 5 seconds then up to 3000 rpm at 300 rpm/s for 30 seconds. It is then baked on a hot plate at 180° C. for 5 minutes followed by a cool down. Then, an AZ-5214-E resist is spun on at 5000 rpm for 30 seconds and baked on a hot plate at 95° C. for 2 minutes. The resist is exposed for 8 seconds at 200 mJ/cm$^2$ using a dark field connection lines mask and then developed for 3-7 minutes in MF CD-26 developer. The developed resist is rinsed in water and blown dry with nitrogen gun. The chromium and gold layers are then thermally evaporated on the patterned resist. The metal layers are lifted off in Nano Remover PG at 60° C. for 40 minutes followed by a rinse in IPA, then in DI water, followed by a gently blow dry with a nitrogen gun.

Alternatively, rather than using the lift-off process, the interconnection 21 and pads 23, 25 may be formed by depositing a metal layer, forming a photosensitive layer (such as AZ 5214-E photoresist) on the metal layer, photolithographically exposing and developing the photosensitive layer and patterning (i.e., etching) the metal layer using the developed (i.e., patterned) photosensitive layer as a mask. The etching of the gold layer should be conducted quickly, such as for about 5 seconds, to avoid damage to the underlying layers.

Figure 7G:
Figure 8A:
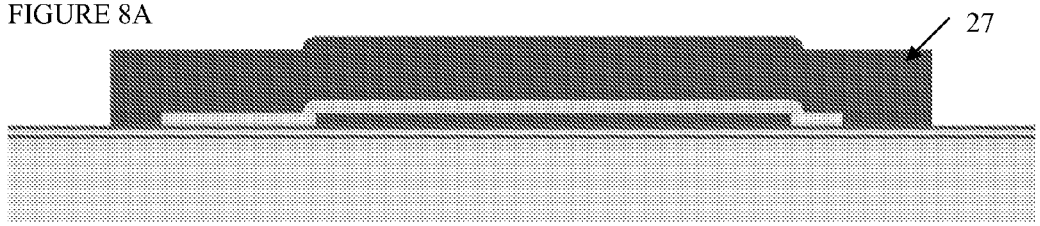

FIG. 7G shows formation of a second polymer layer 27, such as a 10 µm thick layer of SU-8 2010 over the interconnection 21 and pads 23, 25. Layer 27 should be thick enough to act as a cantilever portion of the probe. Thus, layer 27 may be 5 to 100 microns thick and may be made of materials other than SU-8. FIG. 8A shows exposure and development of the SU-8 2010 layer 27 such that it covers the interconnection 21 and pads 23, 25. Layer 27 may be formed by pouring SU-8 2010 equally over the surface, spinning up to 500 rpm at 100 rpm/s for 5 seconds, then up to 3000 rpm at 300 rpm/s for 30 seconds and soft baking at 65° C. for 1 minutes then at 95° C. for 2 minutes. Layer 27 is then exposed at 150 mJ/cm$^2$ for 6 seconds using a mask followed by a post bake at 65° C. for 1 minute then at 95° C. for 2 minutes while avoiding rapid cooling. The SU-8 layer 27 is then developed in SU-8 developer for 2.5 minutes and rinsed in IPA.

Figure 8B:
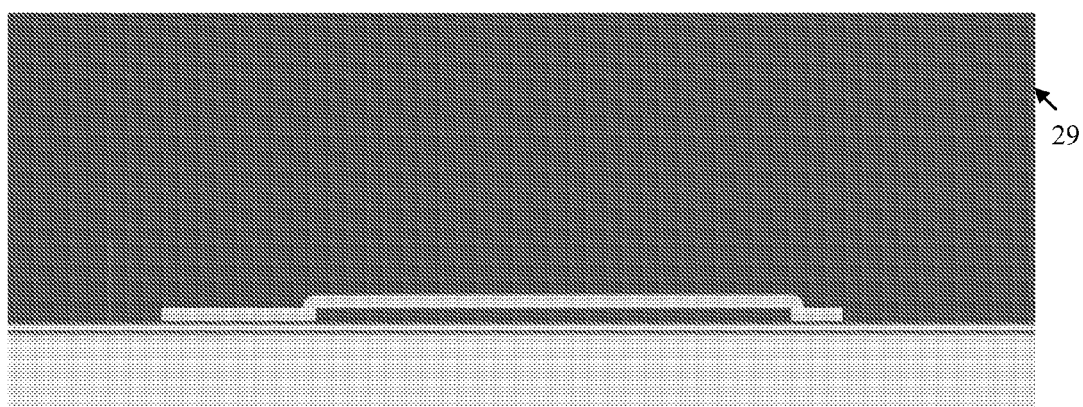
Figure 8C:
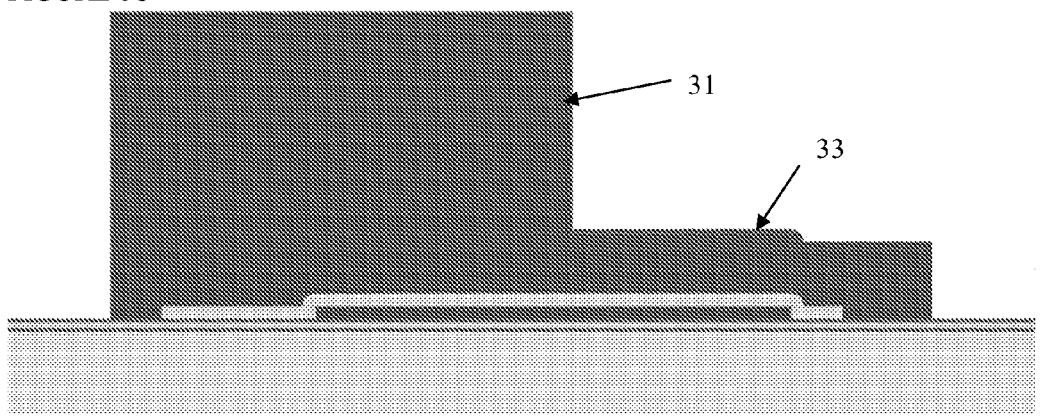

FIG. 8B shows the formation of a third polymer layer 29 over the second polymer layer 27, such as a 100 µm thick layer of SU-8 2100. Layer 29 should be thick enough to act as a cantilever support (i.e., handle) for the probe. Thus, layer 29 may be 75 to 500 microns thick and may be made of materials other than SU-8. FIG. 8C shows exposure and development of the SU-8 2100 layer 29 to form the handle 31 which supports the polymer cantilever portion 33 of the probe. Layer 29 may be formed by preheating the SU-8 2100 at 65° C. in the bottle so it is more fluid, pouring the SU-8 2010 as equally as possible over the surface with a syringe and then heating the wafer at 65° C. to let the resist flow equally. If desired, bubbles may be removed with the back handle of a Q-tip or other implement. After layer 29 reaches room temperature, it is spun up to 500 rpm at 100 rpm/s for 5 seconds then up to 3000 rpm at 300 rpm/s for 30 seconds and soft baked at 65° C. for 5 minutes then at 95° C. for 20 minutes. Layer 29 is then exposed at 500 mJ/cm$^2$ for 20 seconds through a mask and post baked at 65° C. for 1 minute then at 95° C. for 10 minutes while avoiding rapid cooling. It is then developed in SU-8 developer for 18 minutes and rinsed in IPA.

Figure 8D:
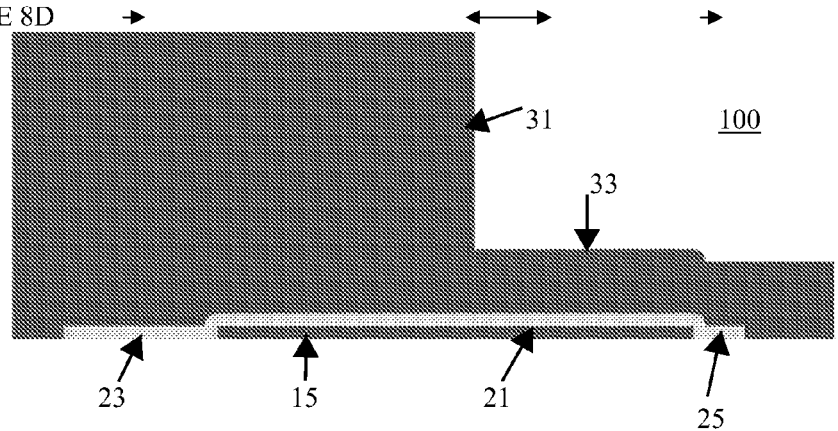

FIG. 8D shows the final probe 100 release from the substrate 11 by a selective chrome etch to selectively remove the release layer 13. Different release layer 13 materials which may be selectively etched with respect to the polymer and substrate 11 materials may also be used. The release may be conducted by curing the wafer on a hot plate at 180° C. for 10 minutes to mechanically stabilize the SU-8, immersing the wafer in a chromium etchant for about 10 minutes and removing the floating probes with tweezers or other instruments. The probes are then rinsed in water and carefully blow dried with nitrogen. Thereafter, the recording electrodes, such as those shown in FIG. 4, are formed on the recording pad(s) 23 and the external electronics are connected to the contact pad (s) 25. The interconnect 21 is encapsulated between the polymer layers in the cantilever 33 and the handle 31. The recoding pad(s) 23 are exposed in the surface of the polymer cantilever 33 while the contact pad(s) 25 are exposed in the surface of the polymer handle 31.

FIGS. 9-12 illustrate another aspect of the second embodiment. In this aspect of the second embodiment, Parylene-C, a bio-compatible polymer, is used to build the neural probe. Parylene has been widely used in several biological applications and is also already used in the context of neurobiology. Therefore, the biocompatibility of parylene is already proven. Parylene has an exceptional property of being able to be deposited into a conformal layer and is well known to contain a minimal number of pinholes, even in very thin layers.

However, since parylene is not photolithographically patternable, additional complexity arises in the fabrication process. In other words, parylene is not photosensitive. Thus, a separate photosensitive layer, such as a photoresist, is needed to pattern parylene. Furthermore, unlike the SU-8 process described above, to pattern parylene, a hard mask is preferably utilized. However these extra steps should not significantly affect the cost of such a probe.

Figure 9A:
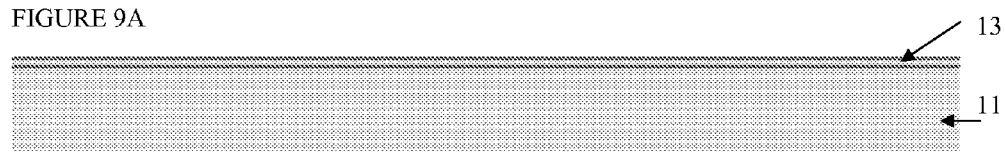
FIGS. 9A-9F, 10A-10F, 11A-11D and 12A-12B are side cross sectional views of steps in a method of microfabricating another neural probe of the second embodiment.
Figure 9B:
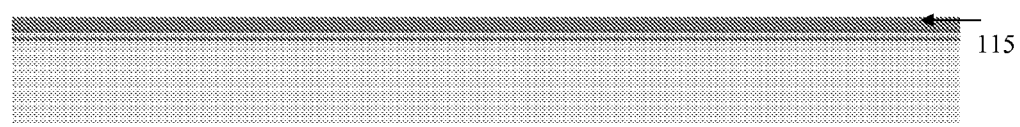
Figure 9C:
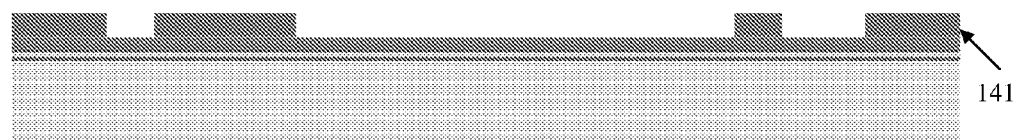

The multi-step fabrication of a parylene based multi-electrode neural probe is illustrated in FIGS. 9A to 12B. FIG. 9A shows a substrate 11, such as a silicon wafer covered with a release layer 13, such as a thermally evaporated 50 Å Cr/500 Å Au/200 Å Cr release layer. FIG. 9B shows deposition of a non-photosensitive polymer layer 115, such as a 0.5 µm Parylene-C layer. Other polymer materials and thicknesses may be used. FIG. 9C shows photoresist 141 spinning and patterning over the polymer layer 115.

Figure 9D:
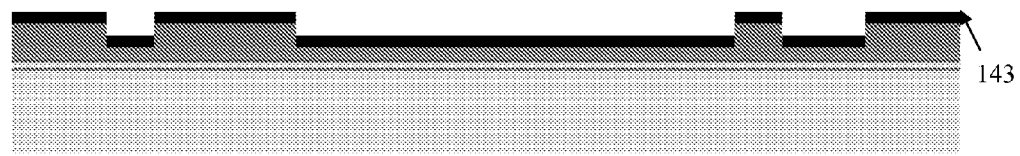
Figure 9E:
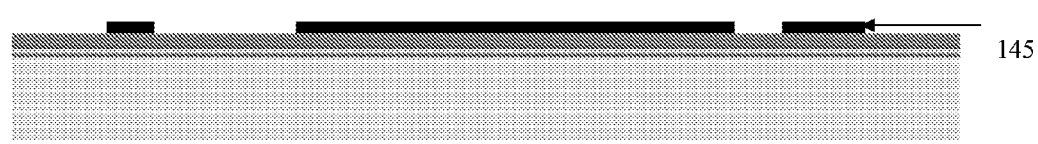

FIG. 9D shows the formation of a first hard mask layer 143, such as thermal evaporation of 2000 Å of aluminum. Other metals, as well as oxides and nitrides, for example may be used as a hard mask which may be used as an etching mask for etching of parylene. FIG. 9E shows lift-off of the aluminum layer 143 in acetone to form the first etching mask (i.e., the hard mask) 145. The hard mask 145 covers the portion of the polymer layer 115 where the interconnect will be formed in subsequent steps. Alternatively, the hard mask 145 may be formed by forming and patterning the photoresist layer 141 over the aluminum layer 143, and using an etching medium which selectively etches aluminum compared to parylene to form the hard mask.

Figure 9F:
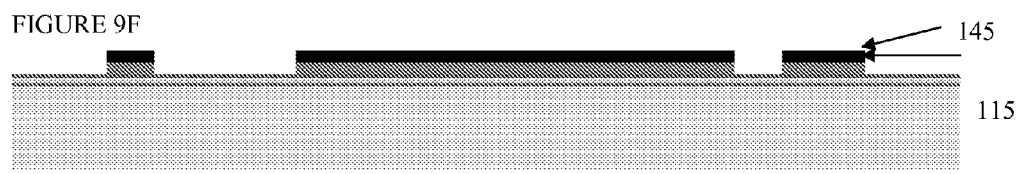
Figure 10A:
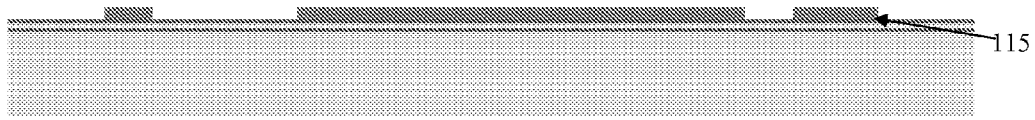

FIG. 9F shows etching of the Parylene-C layer 115 through the first mask 145 using oxygen plasma (200 mT, 400 W) at a rate of 0.2 µm/hour. Other etching media may also be used. FIG. 10A shows removal of the first mask 145, leaving only the patterned parylene cover layer 115 of the neural probe.

Figure 10B:
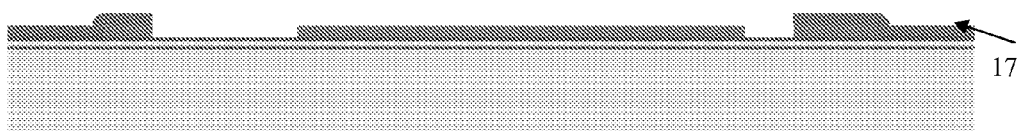
Figure 10C:
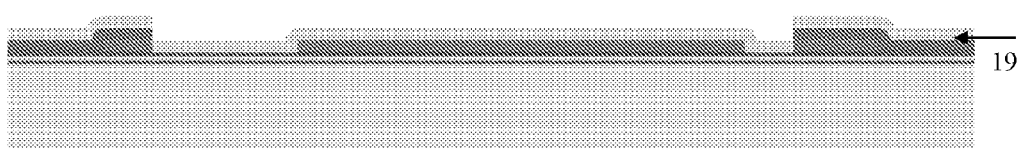
Figure 10D:
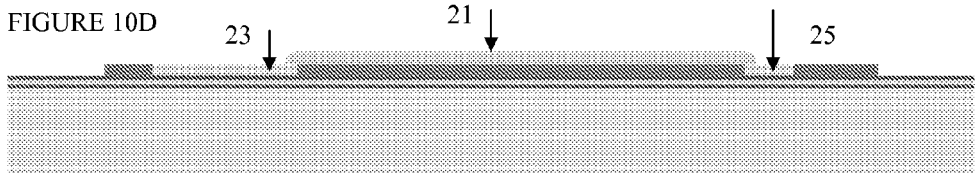

FIG. 10B shows photoresist layer 17 spinning and patterning for forming connecting lines, contact pads and recording pads. This step is similar to the step shown in FIG. 7D. FIG. 10C shows thermal evaporation of a 50 Å Cr adhesion layer and of 0.1 µm Au layer 19 that will be used to form the interconnection and the pads, similar to the step shown in FIG. 7E. FIG. 10D shows lift-off of the gold layer 19 to form the connecting lines 21, the contact pad(s) 23 and recording pad(s) 25, similar to the step shown in FIG. 7F.

Figure 10E:
Figure 10F:
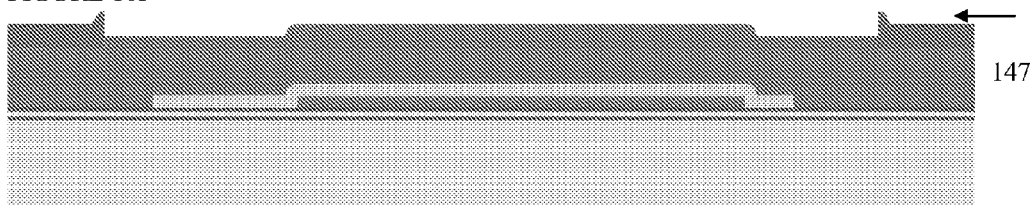
Figure 11A:
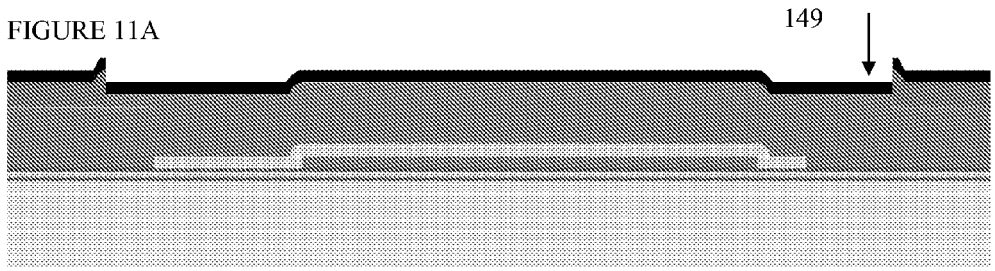
Figure 11B:
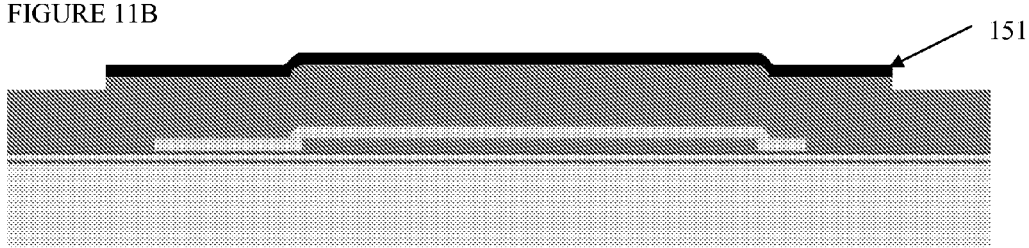

FIG. 10E shows deposition of the second polymer layer 127, such as a 10 µm Parylene-C layer, similar to the step shown in FIG. 7G. FIG. 10F shows photoresist layer 147 spinning and patterning for a second etching (i.e., hard) mask. FIG. 11A shows formation of a second hard mask layer 149, such as thermal evaporation of 2000 Å of aluminum. FIG. 11B shows lift-off of the aluminum layer 149 in acetone to form the second etching mask 151.

Figure 11C:
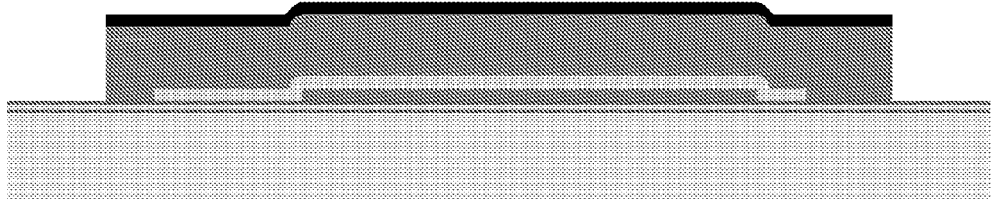
Figure 11D:
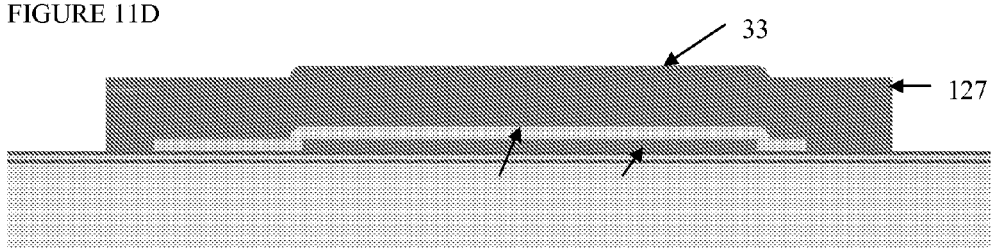

FIG. 11C shows etching of the second Parylene-C layer 127 through the second etching (i.e., hard) mask 151 with oxygen plasma (200 mT, 400 W) at a rate of 0.2 µm/hour. FIG. 11D shows removal of the second etching mask 151, leaving only the patterned parylene layer 127 which comprises the cantilever body 33 of the neural probe as well as a protecting layer 115 for the connecting lines 21. The patterned parylene layer 127 is similar in shape to the patterned SU-8 layer 27 in FIG. 8A.

Figure 12A:
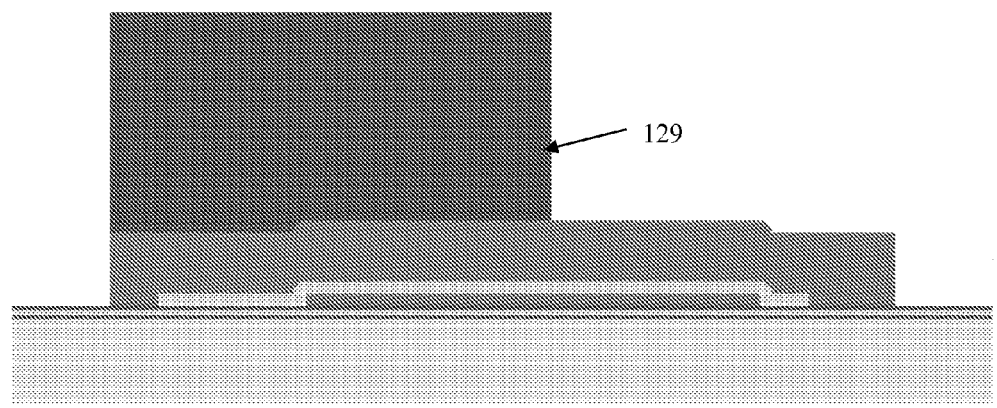
Figure 12B:
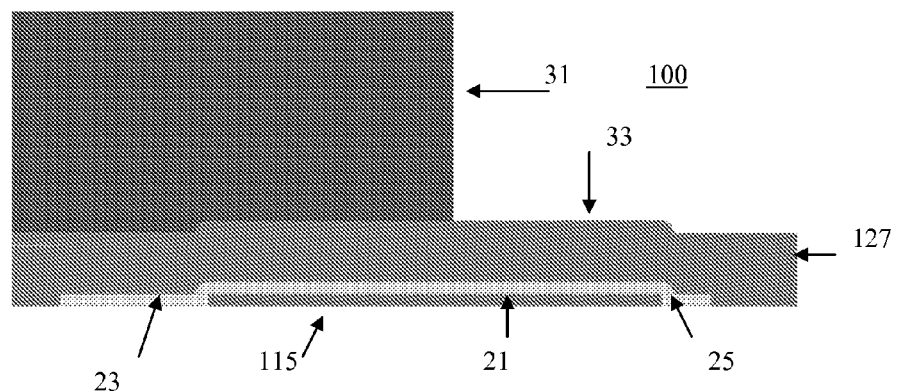

FIG. 12A shows spinning and patterning of thick polymer handle layer 129, such as a 100 µm SU-8 2100 handle layer. This handle layer is similar in shape to the handle layer 29 in FIGS. 8B and 8C. A different polymer material may be used instead. FIG. 12B shows release of the probe from the substrate 11 by selectively etching the Cr release layer 13, similar to the step shown in FIG. 8D.

Thereafter, the recording electrodes, such as those shown in FIG. 4 are formed on the recording pad(s) 23 and the external electronics are connected to the contact pad(s) 25. The interconnection 21 is encapsulated between the parylene layers 115 and 127 in the cantilever 33 and the handle 31. The recoding pad(s) 25 are exposed in the surface of the polymer cantilever 33 while the contact pad(s) 23 are exposed in the surface of the polymer handle 31.

A simplified, exemplary probe layout is shown in FIGS. 13A and 13B. The layout is the same for the SU-8 and parylene based probes. FIG. 13A shows the top view of the probe 100. The probe 100 contains the polymer handle 31 portion, such as an SU-8 2100 handle and a polymer cantilever 33 portion, such as an SU-8 or parylene cantilever, extending from the handle 31. The contact pads 23 are exposed in the top of the handle 31. The recoding pads 25 supporting the recording electrodes are exposed in the top of the cantilever 33. The exemplary probe dimensions are shown in FIG. 13. The cantilever 33 is 10 microns thick, 950 microns long and 140 microns wide. It is attached to a 100 micron thick, 3900 micron long and 300 micron wide second SU-8 cantilever 32. The second cantilever 32 is attached to an SU-8 handle 31. These dimensions may be varied, such as by 10 to 90%, if desired.

FIG. 13B shows the close up view of the cantilever portion 33 of the probe 100 shown in FIG. 13A. The cantilever contains four recording pads 25 connected to interconnections 21. The interconnections may be 2-10 microns wide. The pads 25 may be 50 micron wide square pads separated by 100 microns edge to edge. These dimensions may be varied, such as by 10 to 90%, if desired.

Figure 14:
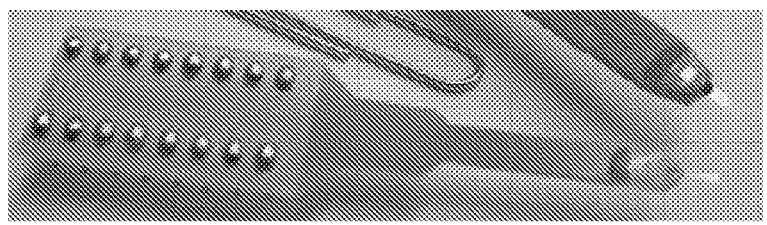
FIG. 14 is a photograph of a circuit board which may be used with the probes of the embodiments of the present invention.

To connect the probe 100 to the electronics used to amplify, detect and/or record the signals from the recording electrodes, the probe 100 is assembled to a printed circuit board. For example, as shown in FIG. 14, the probe 100 is assembled to a circuit board that includes a 16 pins DIP socket (the board shown in FIG. 14 is provided by University of Michigan Center for Neural Communication Technology). Since parylene and SU-8 are rather soft materials, wire bonding between the board and the contact pads may be difficult. To achieve electrical connection between the leads of the SU-8 handle and the printed circuit board, a 3M® Z-axis Conductive Film 5552R or other conducting films, such as ATTA® anisotropic electrically conductive film by Browne Technology may be used. The probe will be bonded to the board using a heat seal bonder according to the process provided by 3M. If desired, epoxy glue may also be used to solidify the link between the board and the probe.

The circuit board is in electrical communication with electronics, such as a computer, a signal amplifier and a voltage or current measurement device, such as volt meter or amp meter which measures a change in voltage or current due to neuron action potentials (i.e., neuron firing) detected by the probe.

If desired, the electronics may also contain a voltage or current source adapted to provide a voltage or current to the electrodes of the probe. The voltage or current may be used to stimulate neuron activity in a living organism, such as a mammal. Thus, the electrode may be used to treat human and other subjects with neurological conditions where it is desired to apply a small voltage or current to a selected affected area, such as a spinal cord injury location.

3. Results of In-Vivo Testing

Figure 15A:
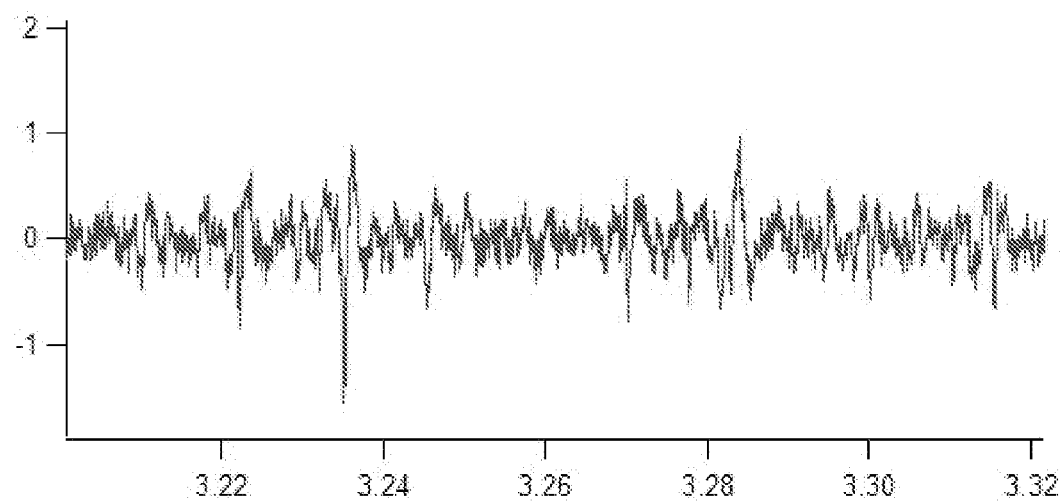
FIG. 15A is a plot of action potential measured with a prior art probe.
Figure 15B:
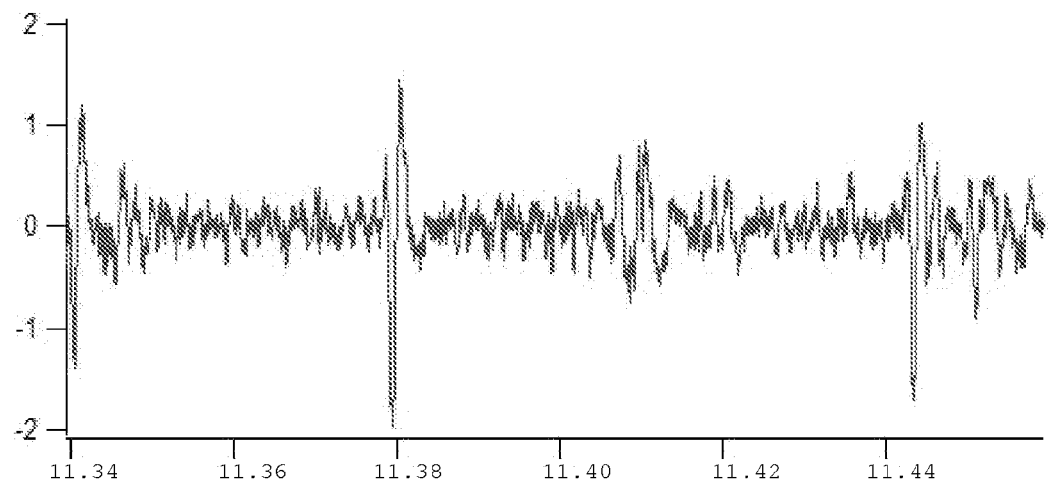
FIG. 15B is a plot of action potential measured with a probe according to an example of the present invention.

The SU-8 probe 100 of the second embodiment was used to detect brain activity of a locust. The analysis of the recording characteristics usually starts with the basic recording properties of a single recording site. The microprobe was advanced through the cortical tissue of the locust brain. The tissue was allowed to settle for several minutes after each step of a record of the neural activity was captured. FIG. 15B shows a record of a SU-8 probe. A prior art probe (provided by University of Michigan Center for Neural Communication Technology) is placed next to the SU-8 probe 100 and records the action potential simultaneously. The data from the prior art probe is shown in FIG. 15A. Similar data are observed from both probes.

Thus, the probe containing the recording electrodes may be record extracellularly, in vivo, the firing of neurons. The probe 100 is provided extracellularly into a living organism and is used for detecting the neuron action potentials, such as neuron firing. If a voltage or current source is provided, then the probe 100 may also be used for stimulating neuron firing activity by providing the probe 100 into a living organism and providing a voltage or current to the electrodes to stimulate the neuron firing activity.

The foregoing description of the invention has been presented for purposes of illustration and description. It is not intended to be exhaustive or to limit the invention to the precise form disclosed, and modifications and variations are possible in light of the above teachings or may be acquired from practice of the invention. The description was chosen in order to explain the principles of the invention and its practical application. It is intended that the scope of the invention be defined by the claims appended hereto, and their equivalents.

The invention claimed is:

1. A neural probe comprising:
   a polymer handle portion made of a first polymer material;
   metal contact pads exposed in the polymer handle portion and presenting an external flat surface;
   a flexible polymer cantilever made from a second polymer material extending from the polymer handle portion;
   a plurality of metal recording pads exposed in the flexible polymer cantilever and presenting a flat external surface, wherein the recording pads are electrically connected to the contact pads via metal conductive interconnections buried in the polymer of the flexible polymer cantilever;
   a polymer layer made of a third polymer material and presenting a flat external surface, wherein the polymer layer is between the recording pads and the contact pads and the metal conductive interconnections are behind the polymer layer away from the flat external surface of the polymer layer;
   wherein the contact pad flat surfaces, the recording pad flat surfaces, and the polymer layer flat external surface are flush with each other; and
   a plurality of elongated metal recording electrodes extending normally from the exposed flat surfaces of the recording pads and separated by a distance, wherein the recording electrodes have a width of 1 micron or less and a height of six microns or less, and wherein a distance between adjacent recording electrodes is 10 microns or less.

2. The probe of claim 1, wherein the distance between adjacent recording electrodes is 1 to 4 microns.

3. The probe of claim 1, wherein the height of the electrodes is in a range of 2 to 5 microns.

4. The probe of claim 1, wherein the width of the electrodes is about 0.1 to about 0.8 microns.

5. The probe of claim 1, wherein the width of the electrodes is about 0.3 to about 0.5 microns.

6. The probe of claim 1, wherein the probe has a probe electrode density of 1/10 nm squared to about 1/50 nm squared.

7. The probe of claim 1, wherein the electrodes have a round cross section.

8. The probe of claim 1, wherein the electrodes comprise sharpened tips.

9. The probe of claim 1, wherein an insulation layer is formed over the electrodes and then the insulation layer is etched back at the electrode tip.

10. The probe of claim 1, wherein the polymer of the flexible polymer cantilever comprises SU-8.

11. The probe of claim 1, wherein the polymer of the flexible polymer cantilever comprises parylene.

12. The probe of claim 1, wherein the polymer handle portion is 75 microns to 500 microns thick.

13. The probe of claim 1, wherein the flexible polymer cantilever is five to 100 microns thick.

14. The probe of claim 1, wherein:
   a circuit board is electrically connected to the probe;
   a voltage or current measurement device which is adapted to measure a change in voltage or current due to neuron action potentials detected by the probe is electrically connected to the circuit board; and
   a voltage or current source adapted to provide a voltage or current to the electrodes to stimulate neuron activity in a living organism is electrically connected to the circuit board.

15. A method of stimulating neuron firing activity comprising providing the probe of claim 14 into a living organism and providing a voltage or current to the electrodes to stimulate the neuron firing activity.

16. A method of detecting neuron action potentials comprising providing the probe of claim 14 extracellularly into a living organism and detecting the neuron action potentials.

* * * * *